(12) United States Patent
Varshavsky et al.

(10) Patent No.: US 12,329,435 B2
(45) Date of Patent: Jun. 17, 2025

(54) TREATMENT APPARATUS

(71) Applicant: Candela Corporation, Marlborough, MA (US)

(72) Inventors: Gary Varshavsky, Natick, MA (US); Dmitry Gregoriev, Framingham, MA (US); Doron Kopel, Zikhron Ya'akov (IL)

(73) Assignee: Candela Corporation, Marlborough, MA (US)

( * ) Notice: Subject to any disclaimer, the term of this patent is extended or adjusted under 35 U.S.C. 154(b) by 694 days.

(21) Appl. No.: 17/736,211

(22) Filed: May 4, 2022

(65) Prior Publication Data

US 2022/0387092 A1 Dec. 8, 2022

Related U.S. Application Data

(60) Provisional application No. 63/195,849, filed on Jun. 2, 2021.

(51) Int. Cl.
*A61B 18/00* (2006.01)
*A61B 18/08* (2006.01)
*A61B 18/14* (2006.01)

(52) U.S. Cl.
CPC .. *A61B 18/082* (2013.01); *A61B 2018/00464* (2013.01); *A61B 2018/0047* (2013.01); *A61B 2018/00898* (2013.01); *A61B 2018/143* (2013.01)

(58) Field of Classification Search
None
See application file for complete search history.

(56) References Cited

U.S. PATENT DOCUMENTS

| | | | |
|---|---|---|---|
| 3,804,314 A | 4/1974 | Gilbert | |
| 6,152,918 A * | 11/2000 | Padilla | A61B 18/22 606/7 |
| 8,211,037 B2 | 7/2012 | Freeman et al. | |
| 9,289,605 B2 | 3/2016 | Choi | |
| 9,364,392 B2 | 6/2016 | Ko | |
| 10,220,195 B2 * | 3/2019 | O'Brien, III | A61M 5/46 |

(Continued)

FOREIGN PATENT DOCUMENTS

| | | |
|---|---|---|
| KR | 20200019399 A | 2/2020 |
| WO | 2016205183 A1 | 12/2016 |

OTHER PUBLICATIONS

Written Opinion of the International Searching Authority for International Application No. PCT/US22/27777 mailed Jul. 12, 2022, five (5) pages.

(Continued)

*Primary Examiner* — Linda C Dvorak
*Assistant Examiner* — Nicholas S Borsch
(74) *Attorney, Agent, or Firm* — Iandiorio Teska & Coleman, LLP

(57) ABSTRACT

A treatment apparatus includes a motorized subsystem in a handpiece housing having a rotating output shaft, an axial cam driven in rotation by the output shaft, and a push rod linearly driven by the axial cam. A cartridge is removably attachable to the handpiece housing and includes a cartridge housing, a needle assembly, a piston in the housing engaging the needle assembly and linearly driven forward by the push rod, and a first biasing member urging the piston rearward.

31 Claims, 15 Drawing Sheets

(56) References Cited

U.S. PATENT DOCUMENTS

| | | |
|---|---|---|
| 2006/0178688 A1 | 8/2006 | Freeman et al. |
| 2012/0158100 A1 | 6/2012 | Schomacker |
| 2014/0128685 A1 | 5/2014 | Na |
| 2015/0182700 A1 | 7/2015 | Bang |
| 2017/0251958 A1 | 9/2017 | Pushpala et al. |
| 2020/0222068 A1* | 7/2020 | Capelli .................. A61B 17/22 |
| 2021/0077350 A1* | 3/2021 | Na ......................... A61N 5/062 |
| 2022/0280076 A1 | 9/2022 | Pushpala et al. |

OTHER PUBLICATIONS

Saudi Authority for Intellectual Property (SAIP) 1st Examination Report for Saudi Arabian Application No. 523451637 mailed Jan. 9, 2025, seven (7) pages.

Japanese Patent Office 1st Office Action for Japanese Application No. 2023-574473 mailed Dec. 9, 2024, five (5) pages.

Written Opinion of the International Searching Authority for International Application No. PCT/US23/35693 mailed Feb. 12, 2024, nine (9) pages.

\* cited by examiner

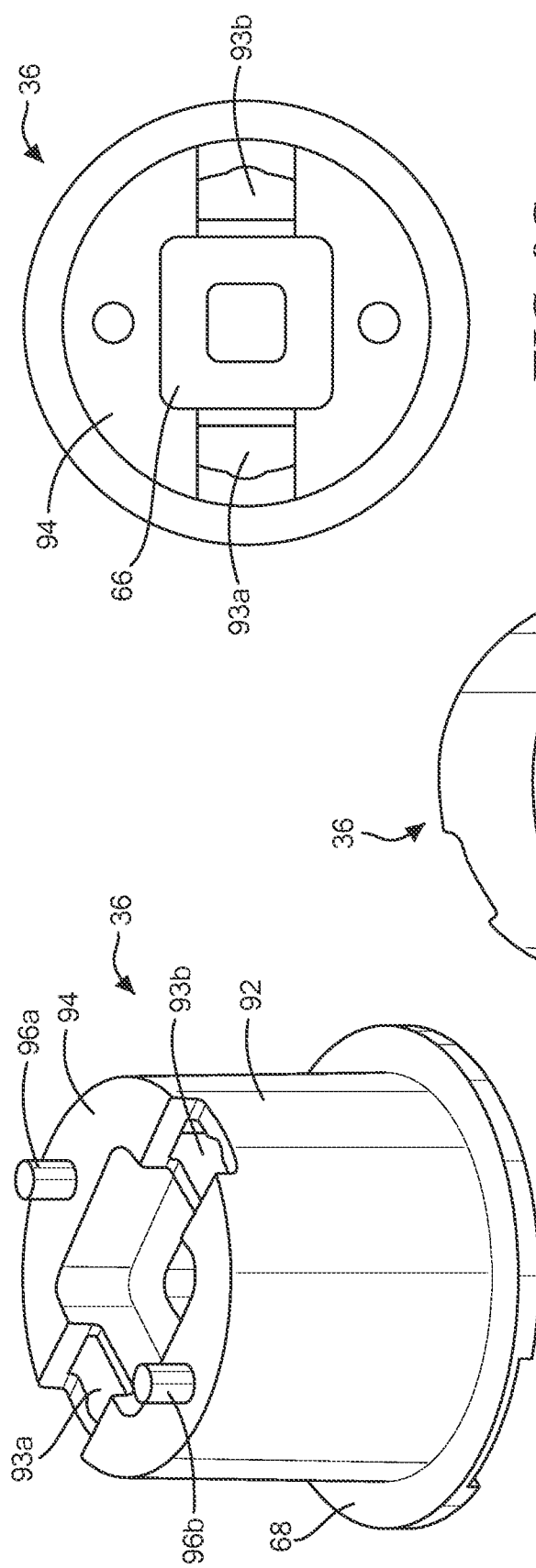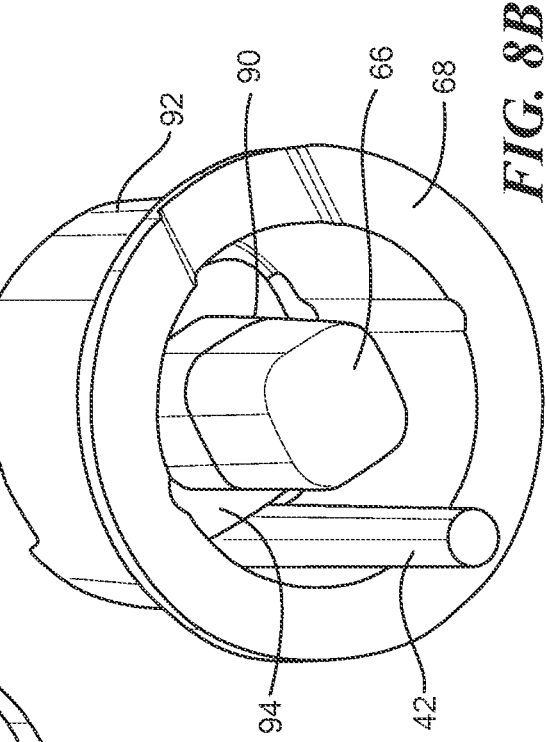

TREATMENT APPARATUS

RELATED APPLICATIONS

This application claims benefit of and priority to U.S. Provisional Application Ser. No. 63/195,849 filed Jun. 2, 2021, under 35 U.S.C. §§ 119, 120, 363, 365, and 37 C.F.R. § 1.55 and § 1.78, and which is incorporated herein by this reference.

FIELD OF THE INVENTION

This invention relates to a treatment apparatus handpiece and cartridge applying RF energy to needles inserted into a patient's skin to treat a variety of conditions including but not limited to wrinkle reduction and cellulite reduction.

BACKGROUND OF THE INVENTION

Skin treatment methods are known whereby needles are inserted to different depths in skin and the subcutaneous area and energized by high frequency energy. See U.S. Pat. No. 9,364,392 incorporated herein by this reference. See also U.S. Pat. No. 10,220,195 incorporated herein by this reference. Motors, solenoids, and the like can be used to drive the needles. Also, various methods are used to electrically connect the needles to the power supply circuitry of the treatment unit.

If a needle cartridge is releasably attached to the treatment handpiece, a new cartridge can be used for each patient. However, engineering challenges include how to drive the needles and how to supply energy to the needles from the handpiece. Typically, in the prior art, a driven shaft in the handpiece extends all the way to the needle assembly.

SUMMARY OF THE INVENTION

Featured is a new treatment handpiece and replaceable cartridge with a very precise arrangement for driving the needles and also featuring a reliable electrical interconnection between the needles and the handpiece. Also featured is a fault subsystem which detects when the needle cartridge has experienced a fault condition. Also featured is a unique cartridge piston arrangement.

Featured is a treatment apparatus comprising a handpiece housing a motorized subsystem in the handpiece housing having a rotating output shaft and an axial cam driven in rotation by the output shaft. A push rod is linearly driven by the axial cam. A cartridge is removably attachable to the handpiece housing and includes a cartridge housing, a needle assembly, a piston in the housing engaging the needle assembly and linearly driven forward by the push rod, and a first biasing member urging the piston rearward.

The motorized subsystem may include a rotary motor driving a gear unit including the rotating output shaft. The needle assembly may include a printed circuit board with an array of needles extending therefrom. The cartridge preferably further includes a front face including guiding orifices therethrough for the needles.

The first biasing member may include a spring between the piston and the cartridge housing. The apparatus may further include a second biasing member urging the push rod rearward such as a spring between the push rod and a push rod guide through which the push rod extends.

The apparatus may further include a piston fault subsystem including, for example, a linear encoder in the handpiece. The piston fault subsystem may further include a pin extending rearwardly from the piston which engages and drives the linear encoder.

One preferred piston includes an inner member surrounded by an outer cylinder and a wall connecting the inner member to the outer cylinder, the wall engaging the needle assembly. The outer cylinder may include a flange. At least one pogo pin may extend between the inner member and the outer cylinder and through the piston end wall. The piston end wall may further include one or more posts extending therefrom connected to the needle assembly printed circuit board. The piston may further include a rearwardly extending post and the cartridge may further include a rear wall including an orifice for the piston rearwardly extending post and an orifice for the at least one pogo pin. The cartridge rear wall may further include at least one rearwardly extending snap hook.

Also featured is a treatment apparatus handpiece cartridge comprising: a housing with a front face and a rear wall; a needle assembly in the housing including a printed circuit board with a plurality of needles extending therefrom through orifices in the front face of the housing; a piston movable relative to the housing rear wall and engaging the printed circuit board for driving the needles; a spring between the piston and the housing front face urging the piston rearward; and a pair of pogo pins extending from the printed circuit board rearward through the piston and the housing rear wall for energizing the needles.

The cartridge may further include a piston fault subsystem such as a pin extending rearwardly from the piston through the housing rear wall for driving a linear encoder.

Also featured is a treatment apparatus comprising a handpiece housing. A motorized subsystem in the handpiece housing includes a rotating output shaft, a cam driven in rotation by the output shaft, a push rod linearly driven by the cam, and a cartridge removably attachable to the housing. One preferred cartridge includes a housing with a front face and a rear wall, a needle assembly in the housing including a printed circuit board with a plurality of needles extending therefrom through orifices in the front face of the housing, a piston movable relative to the housing rear wall and engaging the printed circuit board for driving the needles, a spring between the piston and the housing front face urging the piston rearward, and a pair of pogo pins extending from the printed circuit board rearward through the piston and the housing rear wall for energizing the needles.

The apparatus may further include a piston fault subsystem including a linear encoder in the handpiece. The piston fault subsystem may further include a pin extending rearwardly from the piston and through the housing rear wall and which engages and drives the linear encoder.

The piston preferably includes an inner member surrounded by an outer cylinder and an end wall connecting the inner member to the outer cylinder so the end wall engages the needle assembly. The outer cylinder may include a flange for the spring.

The piston end wall may further include one or more posts extending therefrom connected to the needle assembly printed circuit board. The piston may further include a rearwardly extending post. The cartridge rear wall may further include at least one rearwardly extending snap hook. The motorized subsystem may include a rotary motor driving a gear unit including the rotating output shaft. The apparatus may further include a spring for retracting the push rod.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 8A-8C are schematic views showing an example of a piston within the needle cartridge of FIG. 7;

DETAILED DESCRIPTION OF THE INVENTION

Figure 1:
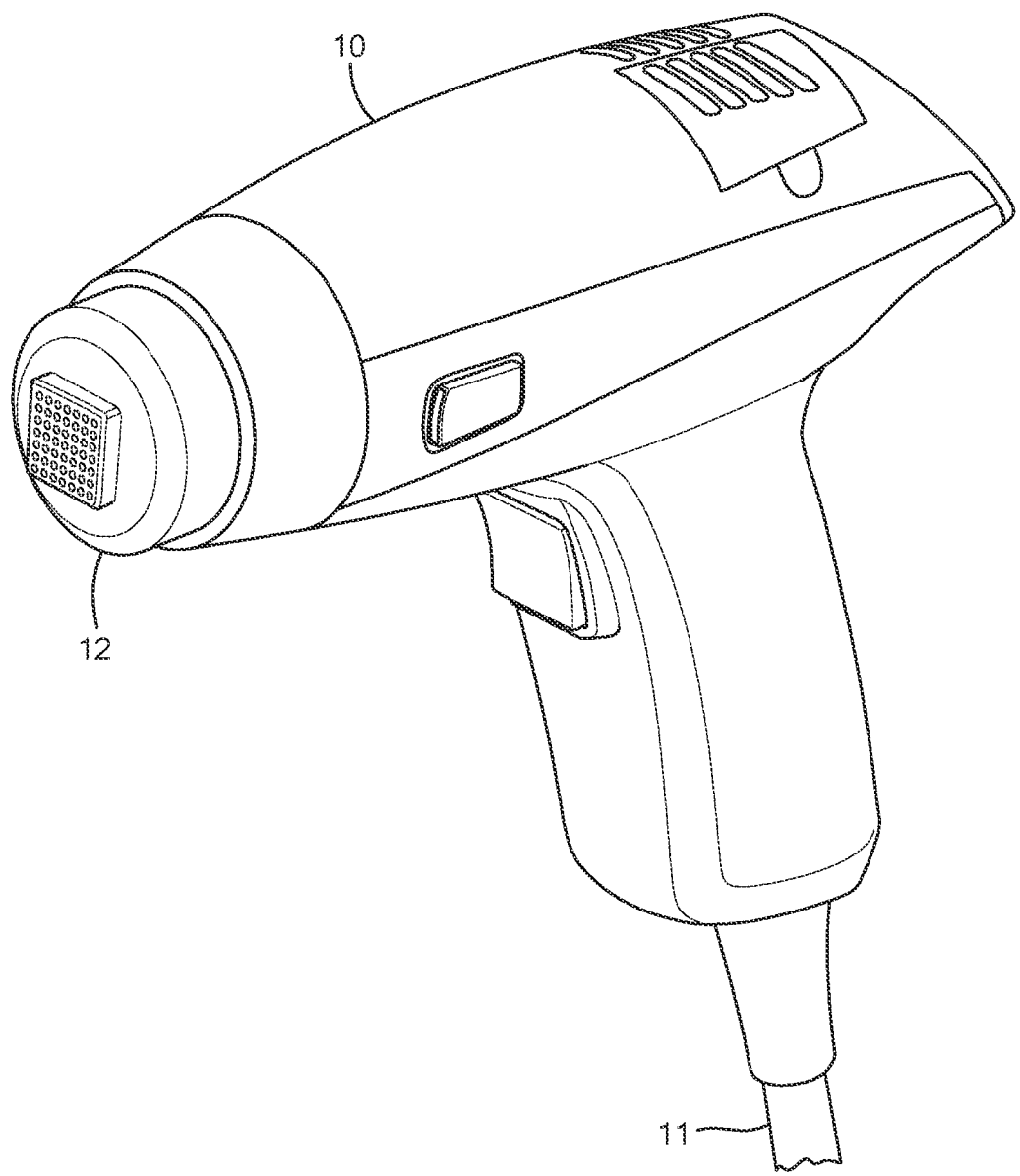
FIG. 1 is a schematic view showing an example of a RF needle treatment handpiece and cartridge.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In one example, a bipolar RF needling skin treatment apparatus includes handpiece 10, FIG. 1 with replaceable cartridge 12. Handpiece 10 is electrically connected to a console housing the appropriate power supply(s), operating processor(s), an input/output section, and the like. The electrical signal is also electrically isolated from the patient and current limited to prevent any harm to the patient. An isolation transformer and current limiter are located in the handpiece.

Figure 2:
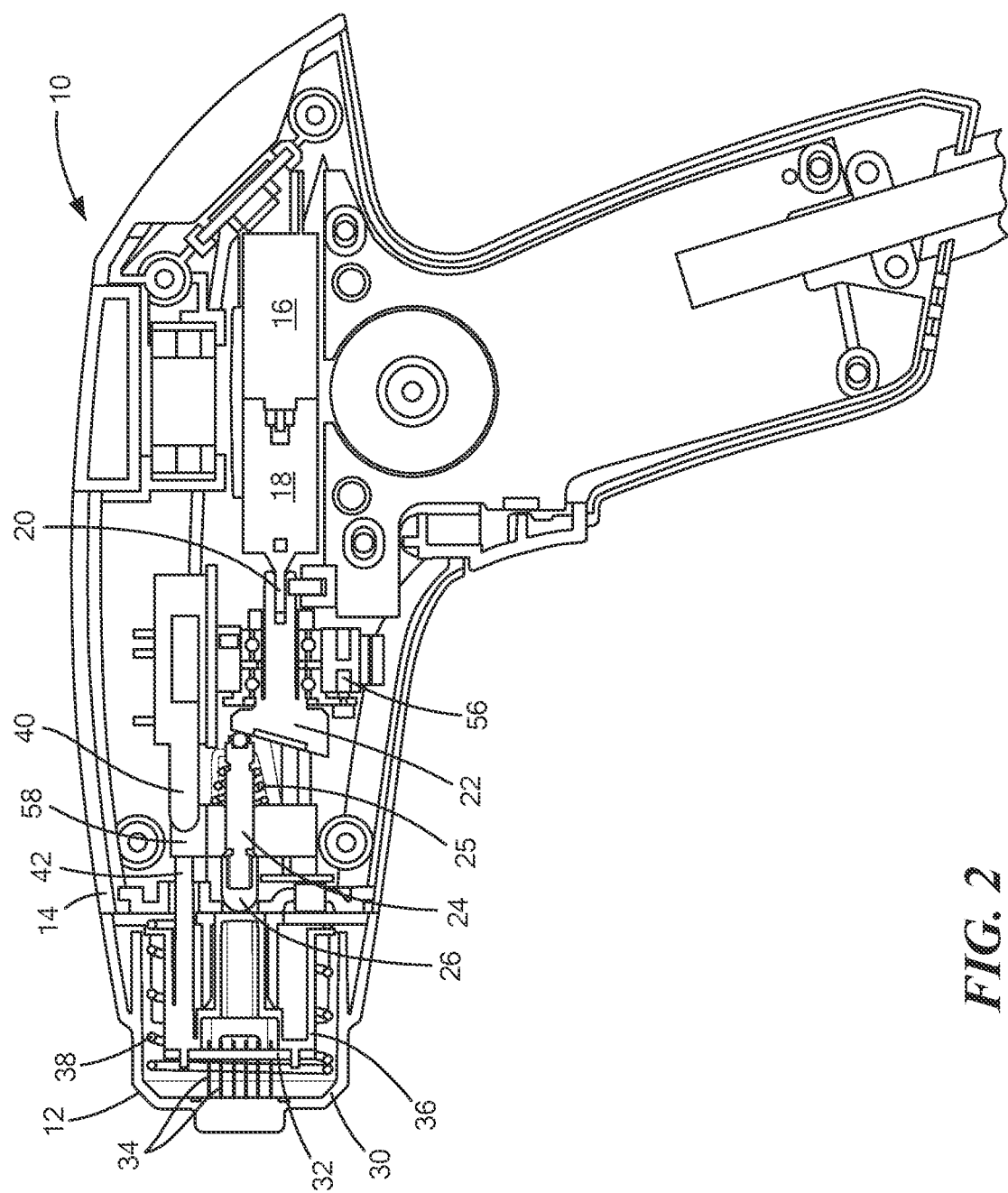
FIG. 2 is a schematic cross-sectional view of the handpiece of FIG. 1 showing the primary components associated therewith.

In this example, handpiece 10 includes housing 14, FIG. 2 and therewithin a motorized subsystem such as DC brushless motor 16 coupled to a driving gear unit 18 having, for example, a gear reduction ratio of 64:1, but depending on the application could have a reduction ratio from 16:1 to 256:1. Gear unit 18 rotates output shaft 20 which drives inline axial cam 22 in rotation to linearly drive push rod 24 which may include plastic (PEEK) tip 26. Spring 25 urges push rod 24 into engagement with cam 22.

DC brushless motor 16 can be driven using a pulse width modulation (PWM) where the rotational velocity of the motor is controlled by adjusting the duty cycle of the PWM input signal. One approach could include 100%, 50%, and 0% duty cycles which correspond to full rotational velocity clockwise, stationary, and full rotational velocity counter-clockwise. Full rotational speed can span the range between 1000 to 10,000 rotations per minute. Torque requirements as well as maximum rotational velocity should be considered when selecting the DC brushless motor 16 and the driving gear unit 18.

Driving gear unit 18 is selected to reduce the rotational velocity of the output shaft 20 which drives the inline axial cam 22. Rotation of axial cam 22 converts to a linear translation of the drive push rod 24. One half rotation of the axial cam 22 provides the full linear drive range of the push rod 24. In one embodiment, the full linear drive range can span from 0 to 3.5 mm and corresponds to the needle insertion depth in tissue. The angular cut on the axial cam 22 can be varied to cover a smaller or larger range of depths, for example full linear drive range of up to 1 mm (52° cut) or up to 10 mm (86° cut). In another embodiment, the full linear drive range can span from 0 to 3.7 mm and corresponds to the needle insertion depth of −0.2 to 3.6 mm in tissue, allowing the needles tips to reside below the front face of the needle cartridge protecting both the treatment providers and the needles.

Figure 13:
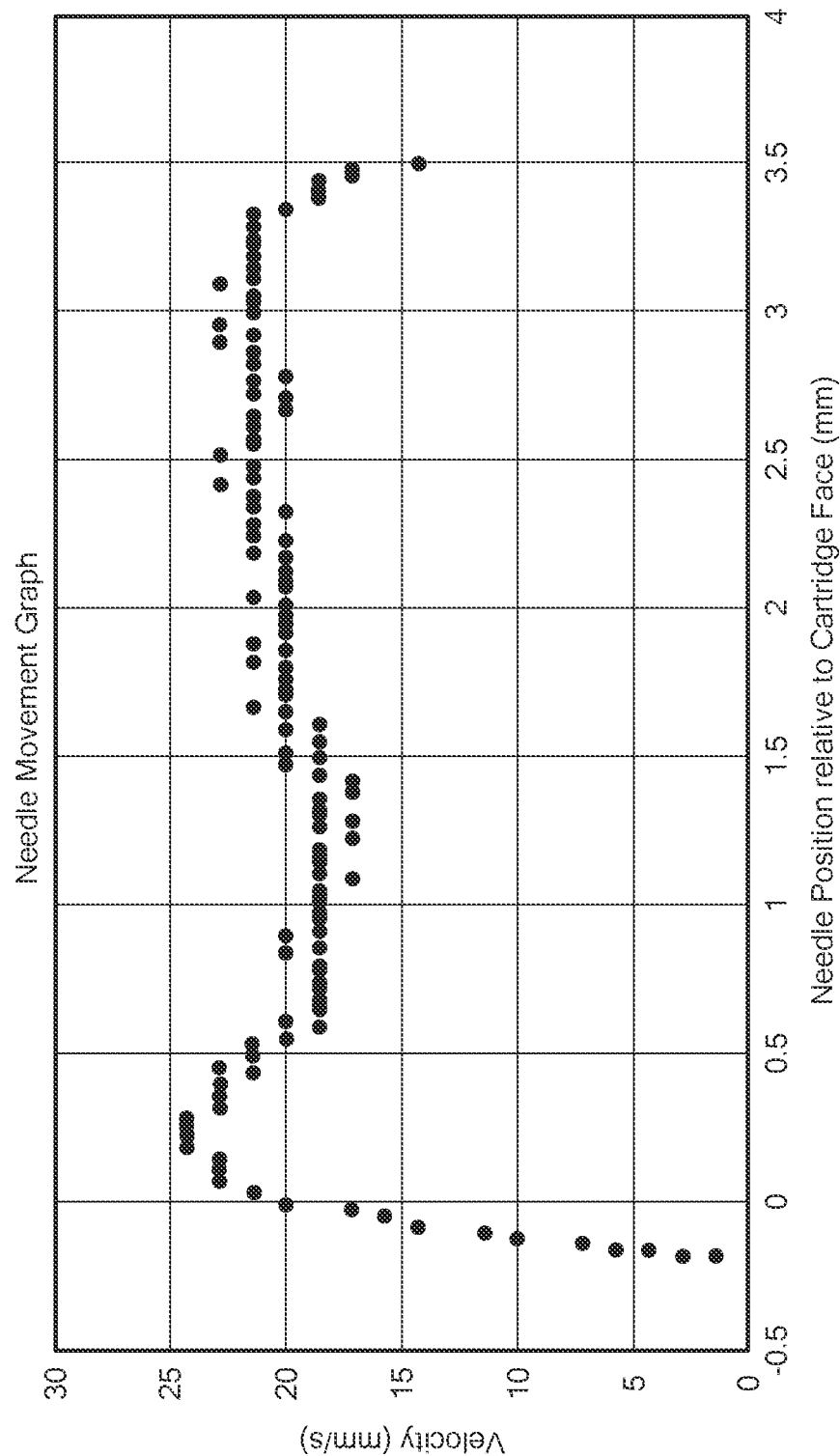
FIG. 13 is a graph showing needle position versus velocity.
Figure 14:
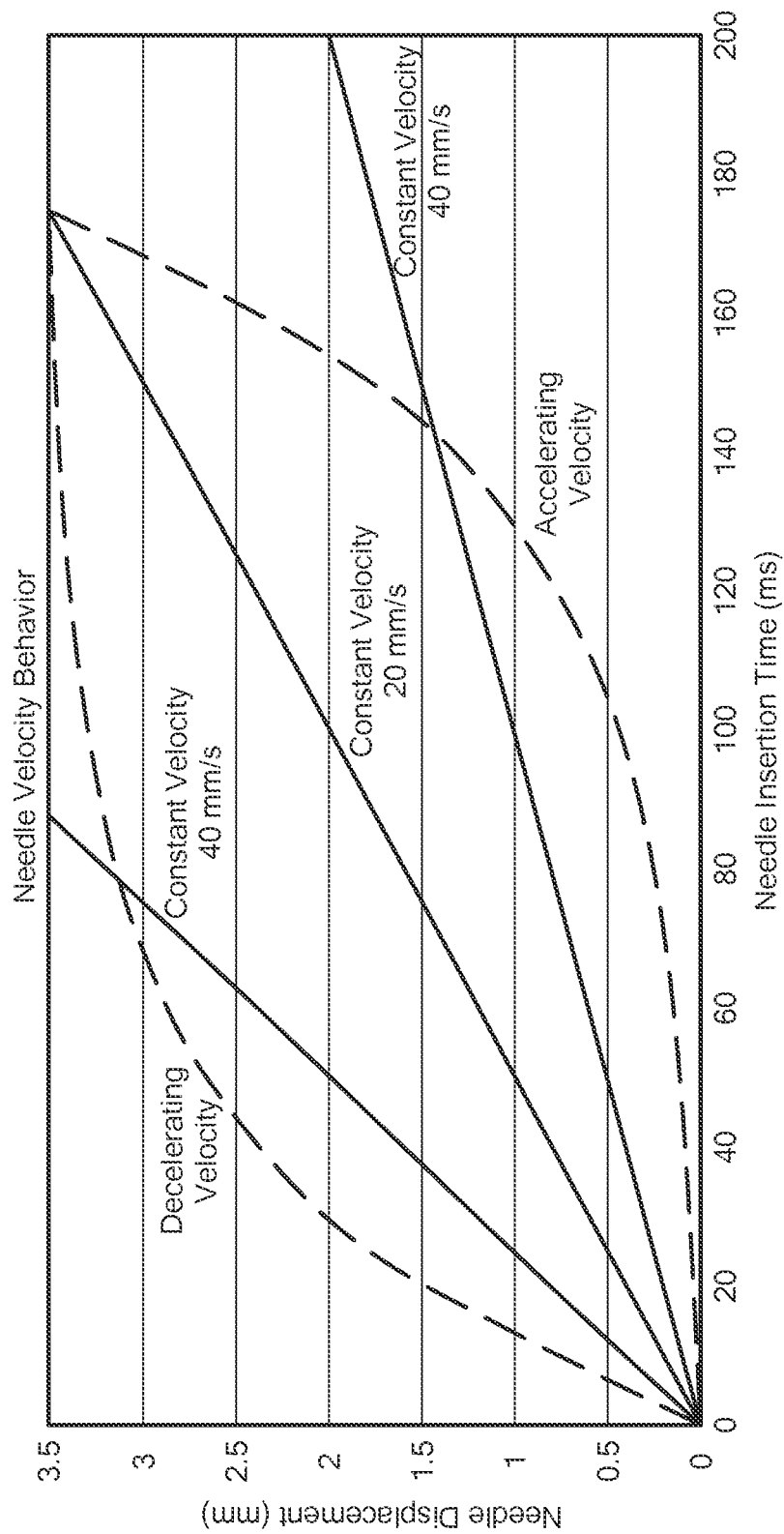
FIG. 14 is a graph showing needle insertion time versus needle displacement.

Needle insertion velocity can be important for ensuring proper needle placement in tissue. When inserting needles in tissue, there are three major forces acting on the needle; penetration force to break the skin surface, frictional force which increases the deeper the needles are inserted in tissue, and cutting forces which are constant with increasing depth for dermis and fatty tissue but larger for dermis compared to fatty tissue. For dermal applications cutting is the major force pushing against the needles. For other applications such as the liver or blood vessels, penetrating the capsule or blood vessel wall are the predominant opposing forces. Because of the various applications, needle insertion velocities can be constant (predominant force is cutting), decelerating (predominant force is penetration), or acceleration (predominant force is friction). For dermal applications, the axial cam 22 is designed to deliver constant velocity shown in FIG. 13. A minimum needle velocity of 20 mm/s may be required to penetrate dermis with preferably faster velocities approaching 50 mm/s when using 34-gauge needles. Larger needles for example 32, 30, and 28 gauge may require successively higher velocities to achieve proper needle placement. Needle placement will be more superficial than desired when needle velocity is lower than the minimal value. Needle velocity can be controlled electrically by setting the PWM duty cycle which adjust the rotational velocity of the axial cam 22. See FIG. 14.

Accelerating/decelerating needles can be controlled electrically or mechanically. For example, ramping the PWM duty cycle up or down during needle insertion accelerates or decelerates the needle velocity. One can imagine a mathematical expression for the ramp which leads to exponential or other functional forms for accelerating or decelerating the needles. Shaping the axial cam 22 is a hardware example for controlling needle insertion acceleration or deceleration. Instead of a straight angular cut defining the cam faceplate 50 which delivers a constant velocity, the cam faceplate 50 could be cut with a functional shape to deliver accelerating or decelerating needles.

The shaft of the microneedles 34 can be insulated such that just the tip of the needle is exposed. For example, just the first 0.6 mm can be exposed but the exposed length can be set from 0.1 mm to 0.6 mm. Insulating material can include parylene, or other polymers such as PTFE. The insulation should also serve as a lubricant to minimize opposing frictional forces during needle insertion and extraction.

Cartridge 12 housing 30 is preferably removably attached to handpiece 10 and preferably includes therewithin a needle assembly, for example, printed circuit board 32 with an array of (e.g., 49) microneedles 34 (e.g., 34 gauge) extending from the printed circuit board through guiding orifices in the front face of cartridge housing 30. The aperture of the guiding orifice in the front face of cartridge housing 30 provides support to the fine 34-gauge needles 34 to prevent buckling of the needles during insertion.

Figure 3:
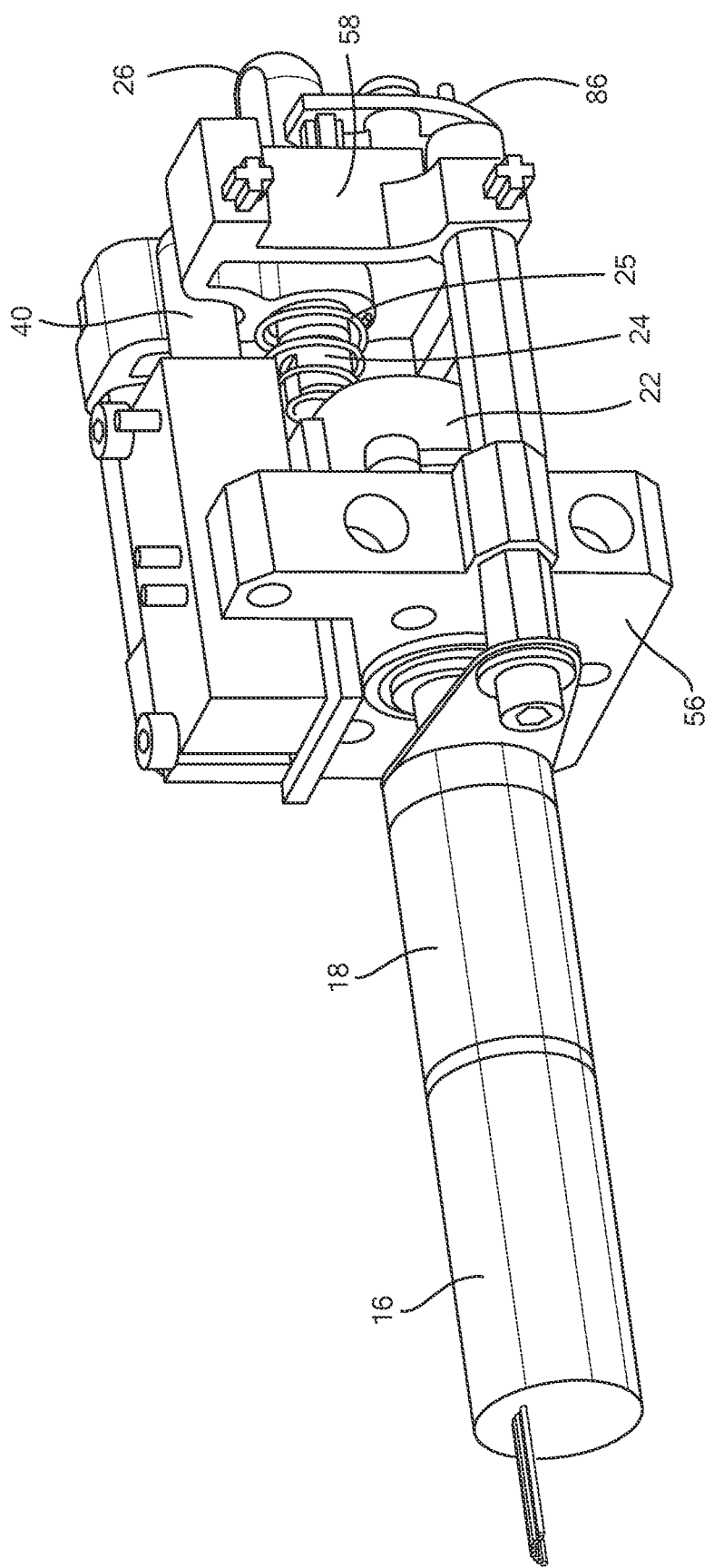
FIGS. 3 and 4 are schematic views showing additional details of the needle assembly drive mechanism of the handpiece of FIG. 2.
Figure 4:
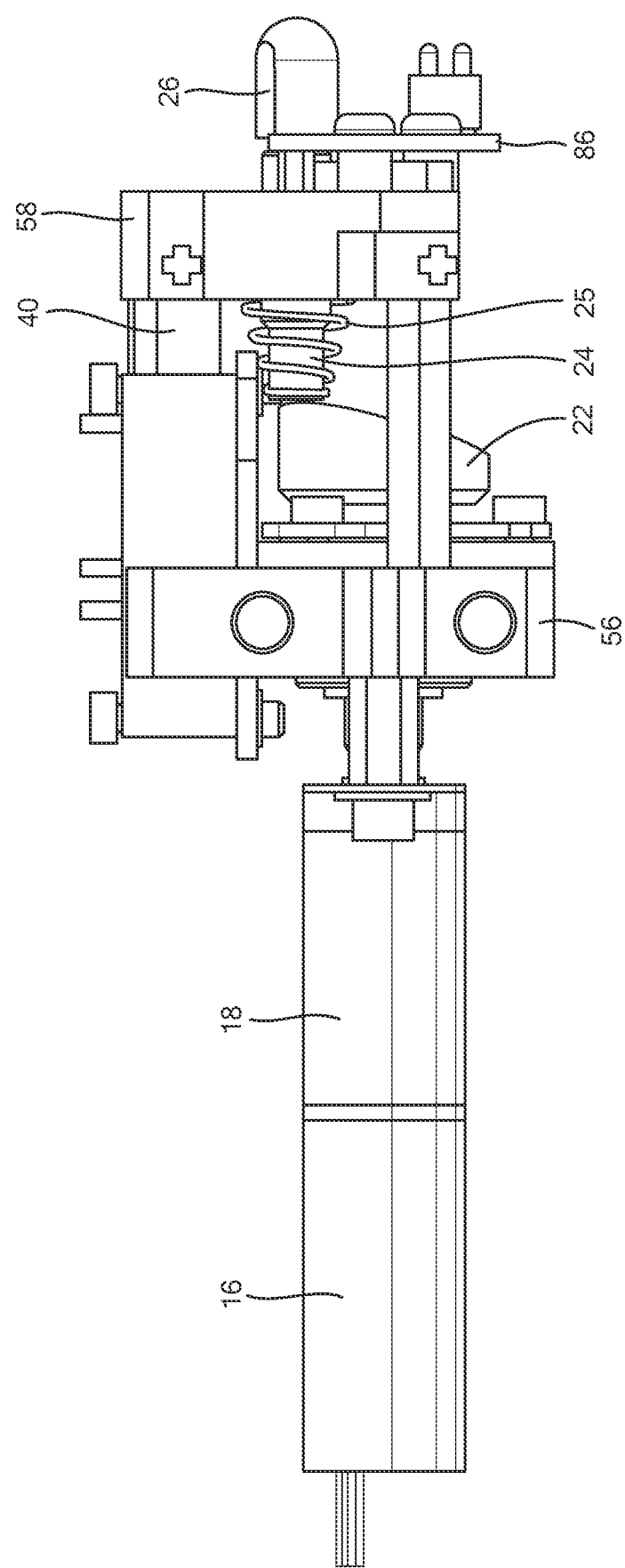
Figure 5:
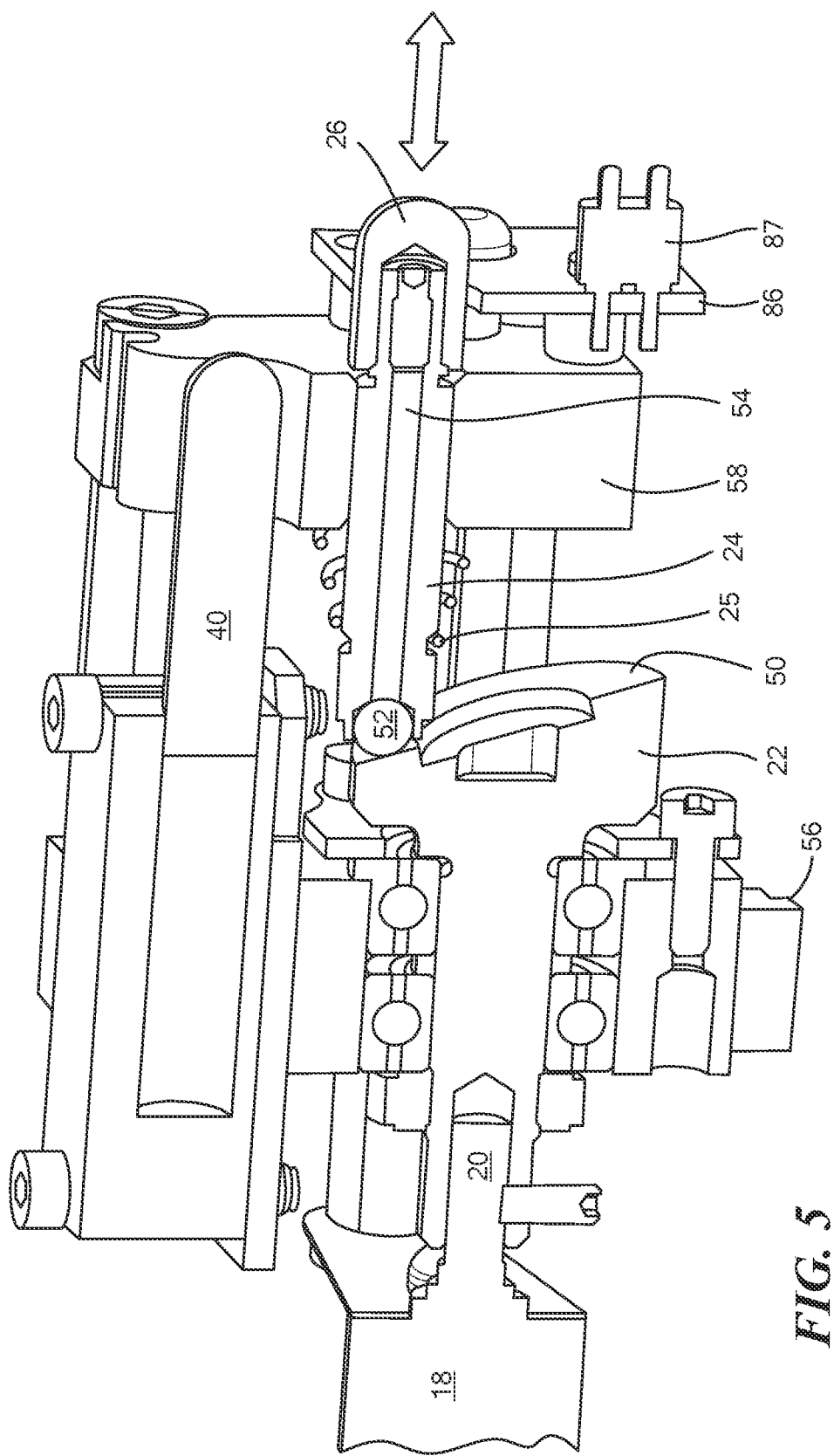
FIG. 5 is another schematic view showing the primary components associated with the needle assembly drive mechanism.

In one example, the needle array has a square footprint of 1 $cm^2$. Piston 36 engages the needle assembly and is linearly driven by push rod 24 within the handpiece. Spring 38 urges the piston rearward. Also featured is a piston fault subsystem including, in this example, a linear encoder 40 in handpiece 10 and pin 42 extending rearward from piston 36 which engages and drives linear encoder 40. See also FIGS. 3-5. Preferably, axial cam 22 includes cam face 50, FIG. 5 which precisely drives push rod 24 in order to ensure precise needle tip insertion depths in the skin. In one embodiment, the cam face may be designed to drive the push rod to a maximum depth of 3.5 mm. In other embodiments, the cam face can be designed to drive the push rod to a maximum of 1 to 10 mm.

In one embodiment where the full linear drive range is set to 3.5 mm, the cam face can drive the needles to a single depth for treating or can drive to a maximum of 3 depths for treating in a single insertion. In another embodiment having a larger full linear drive range of 10 mm, RF energy can be delivered to 1 to upwards of 10 depths within a single insertion. The spacing between treatment depths can be adjusted to deliver individual discrete thermal lesions leaving a gap on unheated tissue between each depth, a single continuous lesion with no gap between each depth, or a combination of the two, where perhaps discrete lesions are desired in the superficial tissue and a continuous lesion in the deeper tissue. The combination of the motor and gear box may be configured such that 60 motor revolutions equates to one rotation of the cam. One or more motor encoders can be used to determine the position of push rod 24. Push rod 24 may include proximal rotating end ball bearing 52 (e.g., 3 mm, stainless steel) engaging cam face 50 and may also include oil filled internal cavity 54 for lubricating bearing 52. Axial cam 22 may rotate relative to bearing housing 56 fixed inside the handpiece and linear encoded 40 and push rod 24 may extend through guide structure 58 also fixed with inside the handpiece. Spring 25 may extend between guide structure 58 and the proximal end 51 of push rod 24.

Figure 6A:
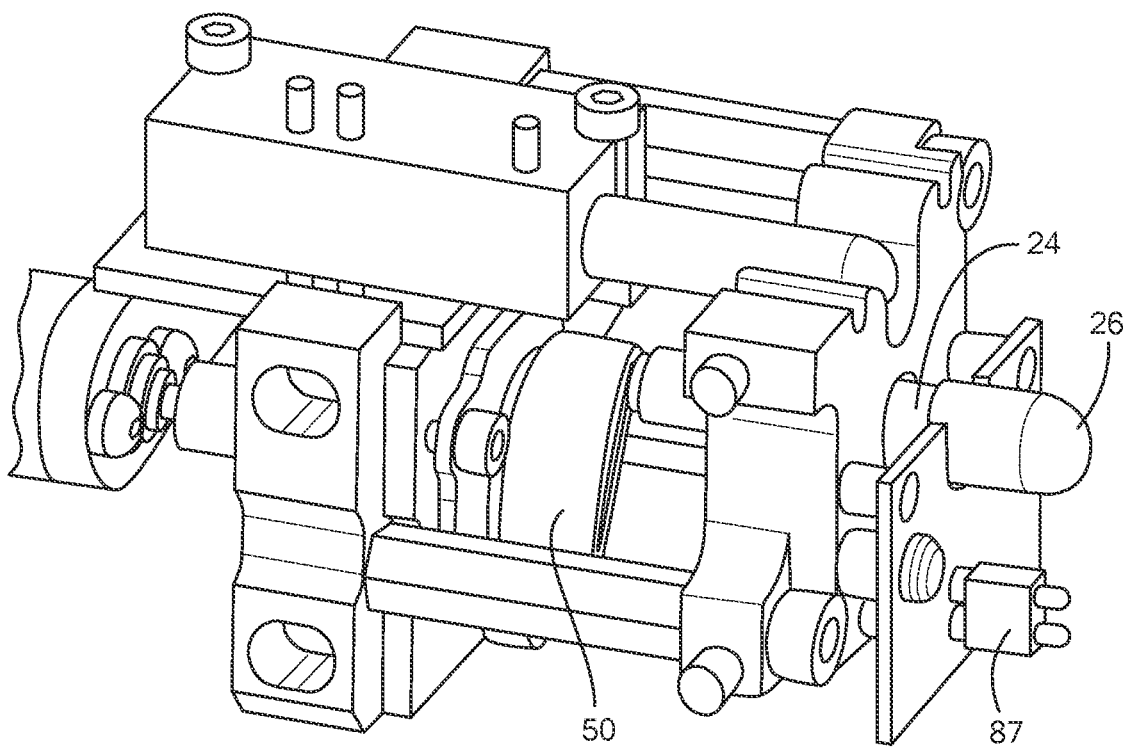
FIG. 6A shows the cam driven push rod driven to a position to insert the needles to one depth into the patient.
Figure 6B:
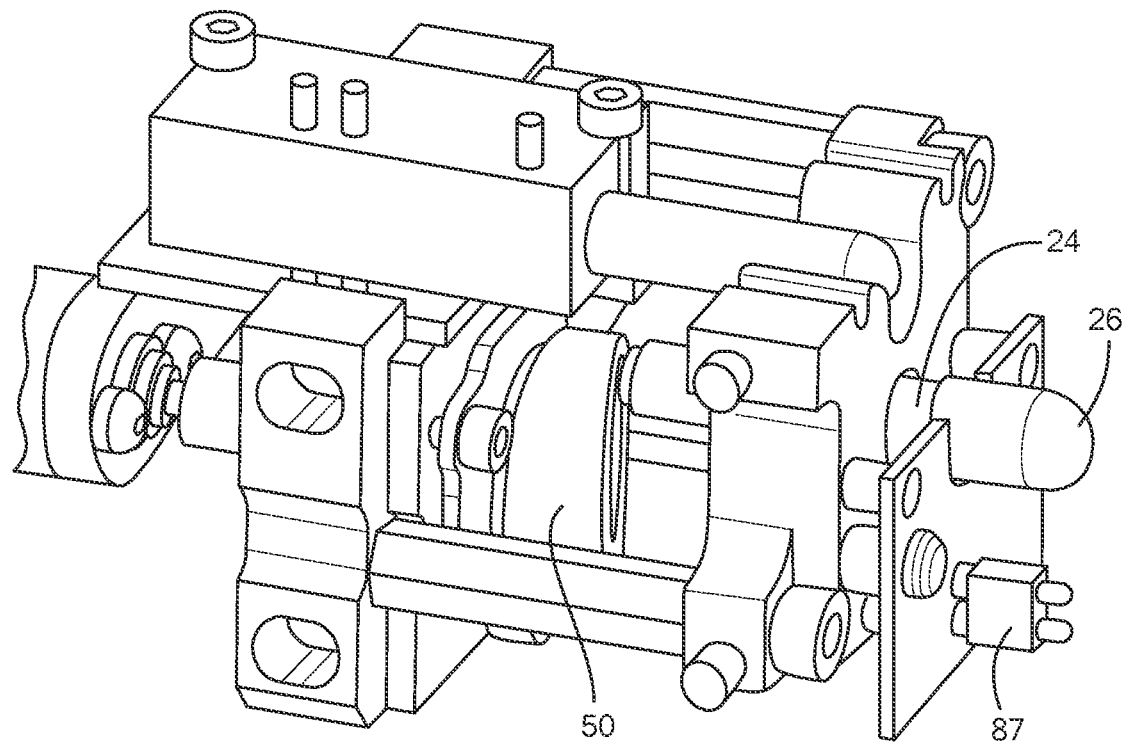
FIG. 6B is a schematic view showing the position of the cam driven push rod for driving the needles to another depth into the patient.
Figure 6C:
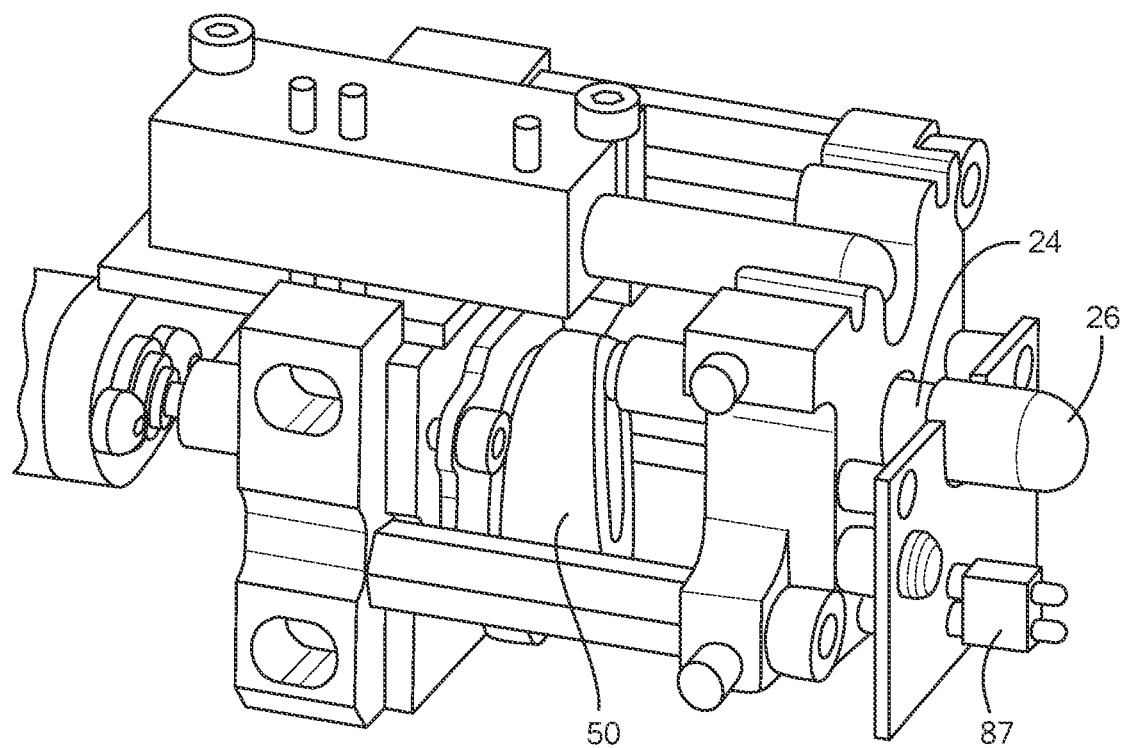
FIG. 6C is a schematic view showing the position of the push rod when the needles are driven to still another depth into the patient.

FIGS. 6A-6C show the rotation of cam face 50 for different needle tip insertion depths. For example, in the position shown in FIG. 6A, push rod 24 will drive the needle tips to an insertion depth of 2.6 mm. In the position shown in FIG. 6B, push rod 24 is in position to drive the needle tips to a dermis depth of 1.8 mm and in FIG. 6C push rod is shown in position to drive the needle tips to a depth of 1 mm. Other needle insertion depths are possible.

Figure 7:
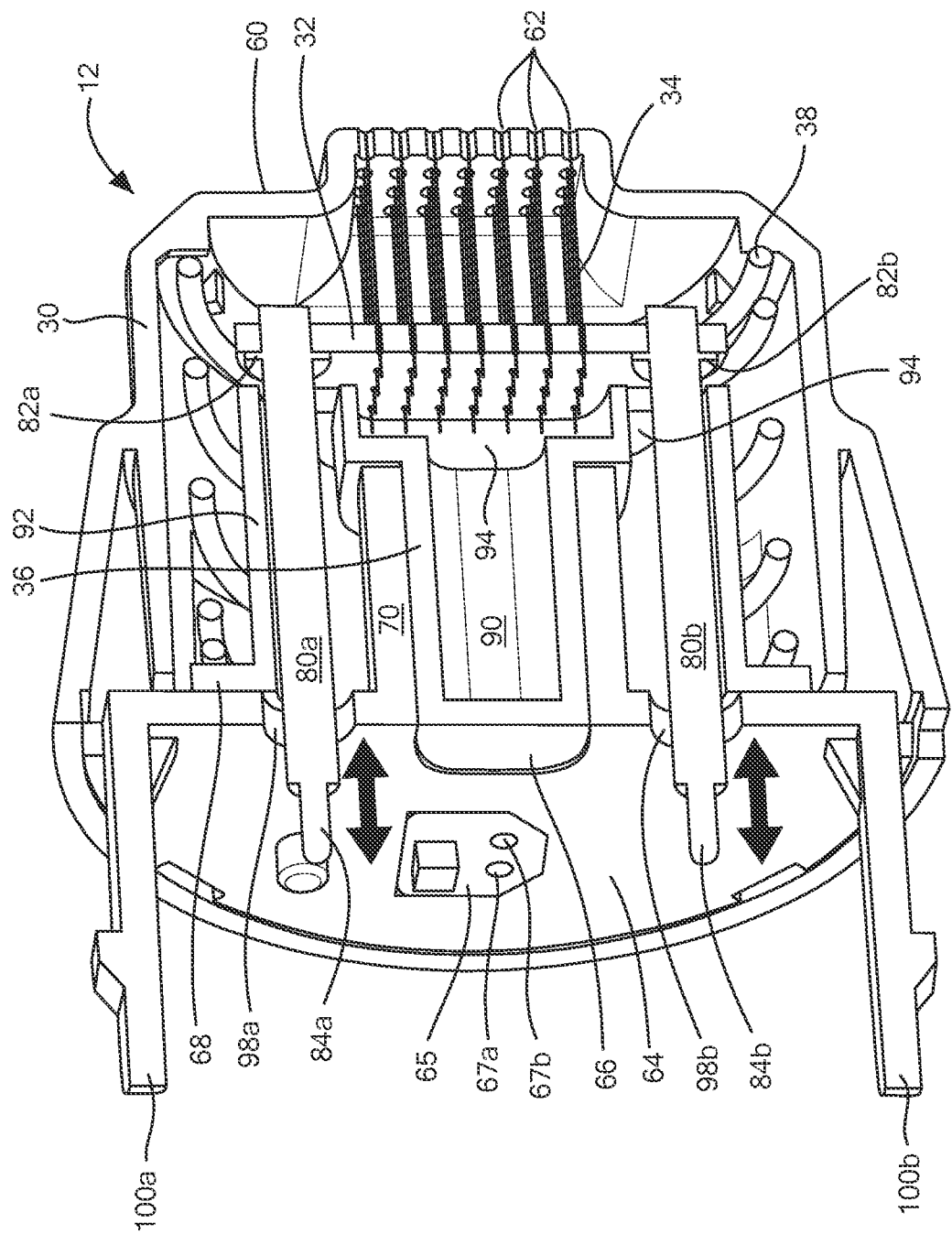
FIG. 7 is a schematic cross-sectional view showing the primary components associated with an exemplary needle cartridge.

As shown more clearly in FIG. 7, needle cartridge 12 housing 30, in one example, preferably include a front face 60 with needle guide orifices 62 and rear wall 64. Piston 36 face 66 is driven by the push rod tip and piston end wall 94 engages and drives printed circuit board 32 and needles 34. Spring 38 extends between housing front face 60 and piston flange 68. Piston 36 resides in and moves relative to rear wall 64 and within rear wall cylinder 70.

Pogo pins 80a and 80b includes ends 82a, 82b, soldered to printed circuit board 32. The pogo pins extend rearward through piston 36 and end wall 64 and spring ends 84a. 84b contact conductive pads on printed circuit board 86, FIG. 5 of the handpiece. In this way, energy from the handpiece is delivered to printed circuit board 32 and needles 34 via pogo pins 80a and 80b. Energy is delivered to handpiece printed circuit board 86 from a console unit with one or more power supplies electrically connected to the handpiece via cable 11, FIG. 1. A cartridge authenticator circuit board 65 is located on wall 65 of cartridge 12 includes an encrypted code which is read by circuit board 86, FIG. 5 via pogo pin unit 87 which establishes electrical contact with lands 67a, 67b, FIG. 7 of circuit board 65 in order to authenticate the replacement cartridge.

Figure 9:
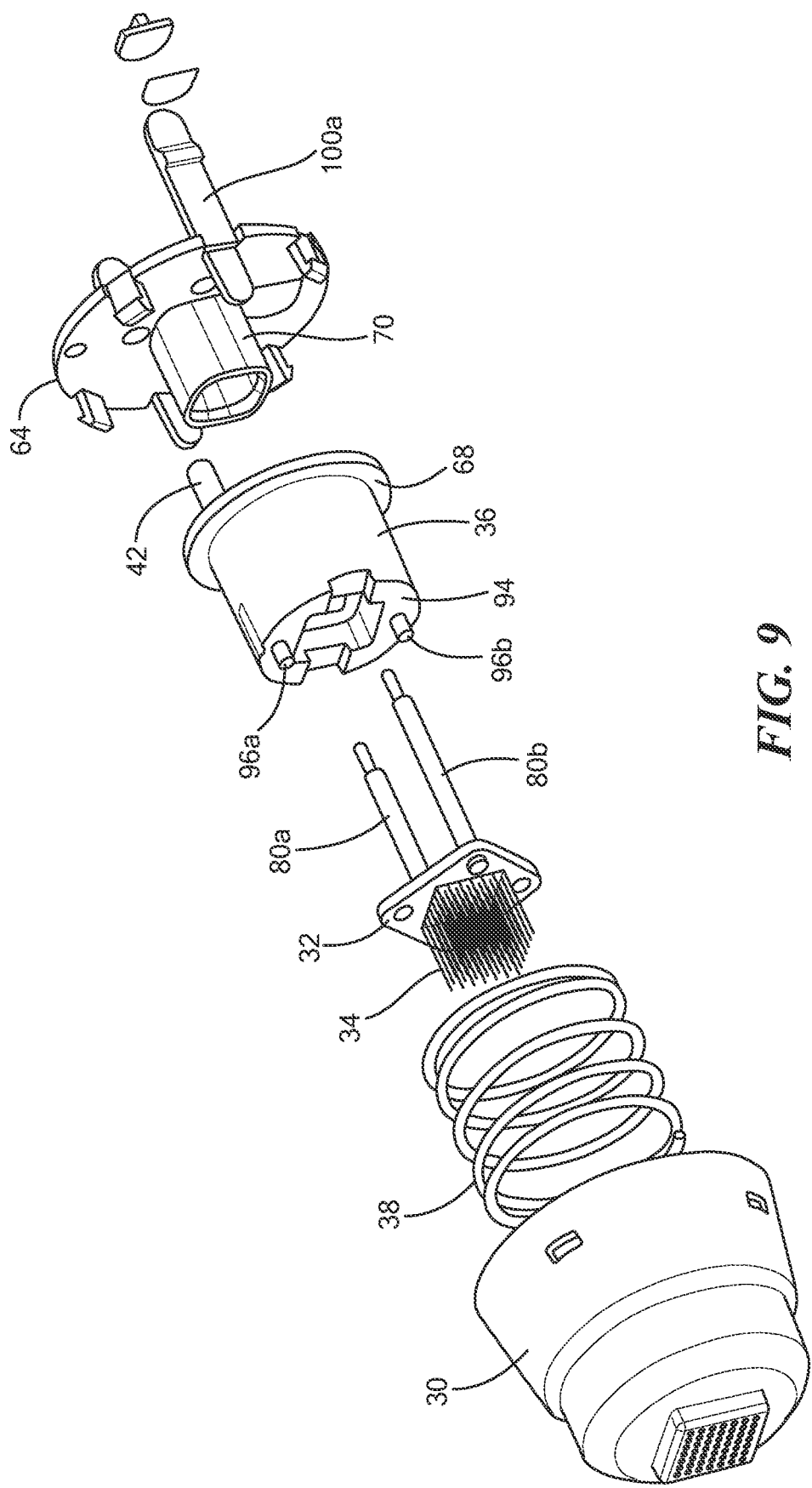
FIG. 9 is a schematic exploded view again showing the primary components associated with an exemplary cartridge subassembly.
Figure 12:
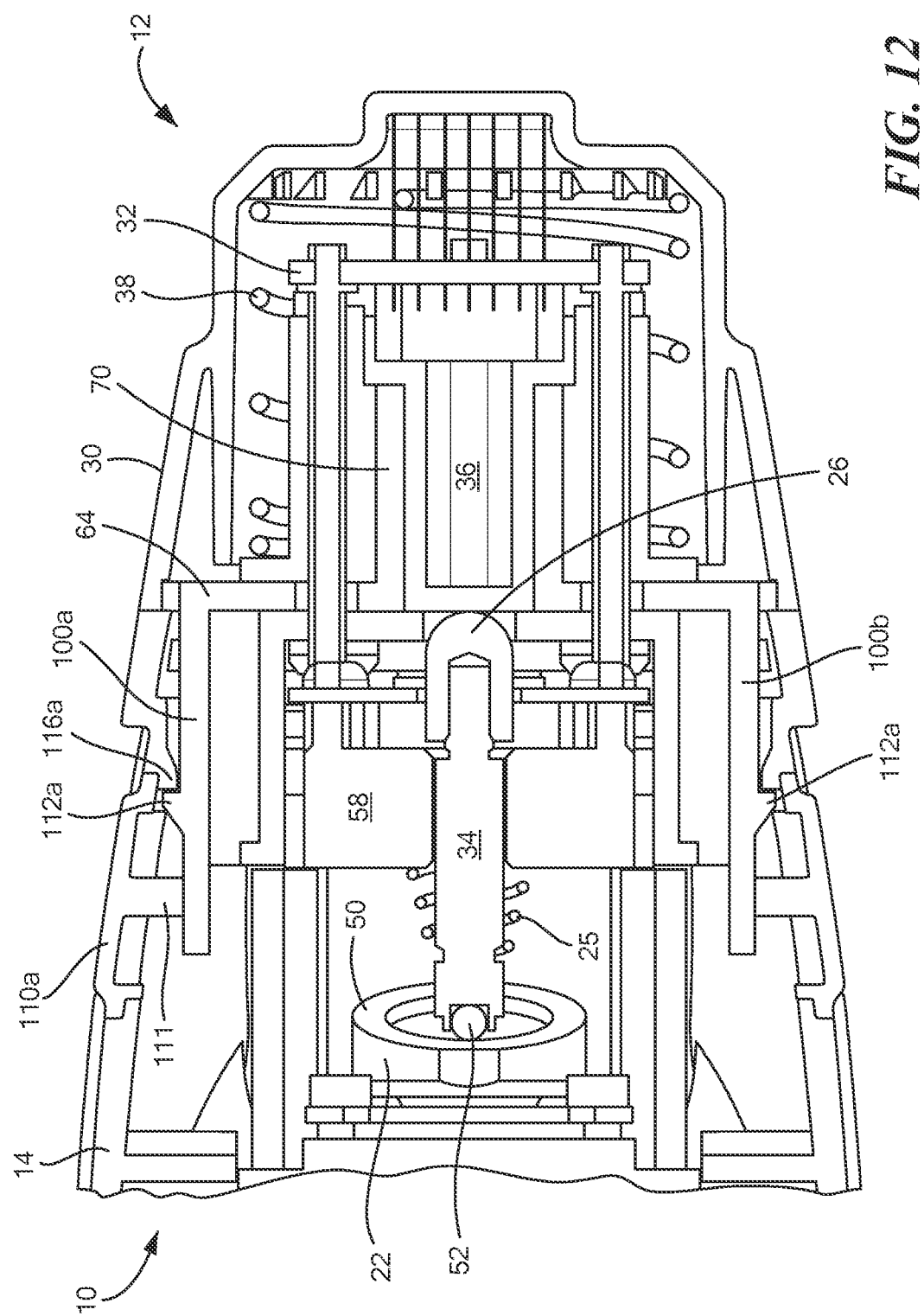
FIG. 12 is another schematic view showing the cartridge assembly attached to the handpiece.

As shown more clearly in FIGS. 8A-8C, piston 36 preferably includes inner member 90 slidable in rear wall cylinder 70 and is surrounded by outer cylinder 92 and functions to drive printed circuit board 32 while allowing the pogo pins to extend between the inner member 90 and the outer cylinder 92 via orifices 93a. 93b in end wall 94 connecting inner member 90 and outer cylinder 92. Outer cylinder 92 flange 68 engages wall 64 and serves as a point of contact for spring 38 as shown in FIGS. 7 and 9. End wall 94, FIG. 7 also includes posts 96a, 06b which can be attached (e.g., hot melted) to circuit board 37. The cartridge rear wall 64, FIGS. 7 and 9-10 includes orifices 98a, 98b for the pogo pins, orifice 98c for the piston pin 42, cylinder 70 for the piston inner member 90, and rearwardly extending snap hooks 100a, 100b releasably securing the cartridge to the handpiece as shown in FIG. 12 where membrane 110 post 111 can be pushed to release the catches 112a of snap hook 100a from corresponding catch 116a of the handpiece housing 114.

Figure 10:
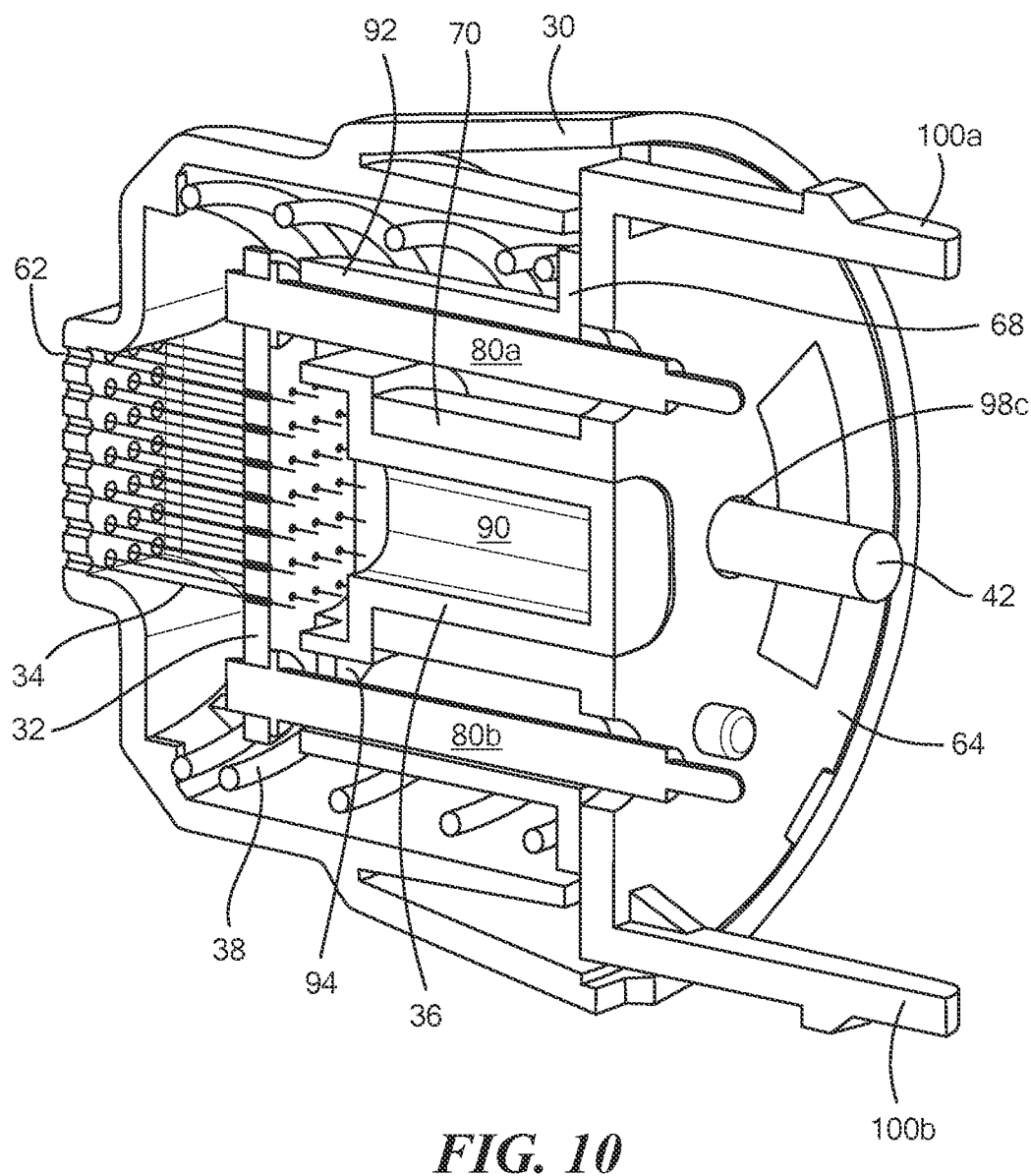
FIG. 10 is another schematic view showing an example of a cartridge assembly.
Figure 11:
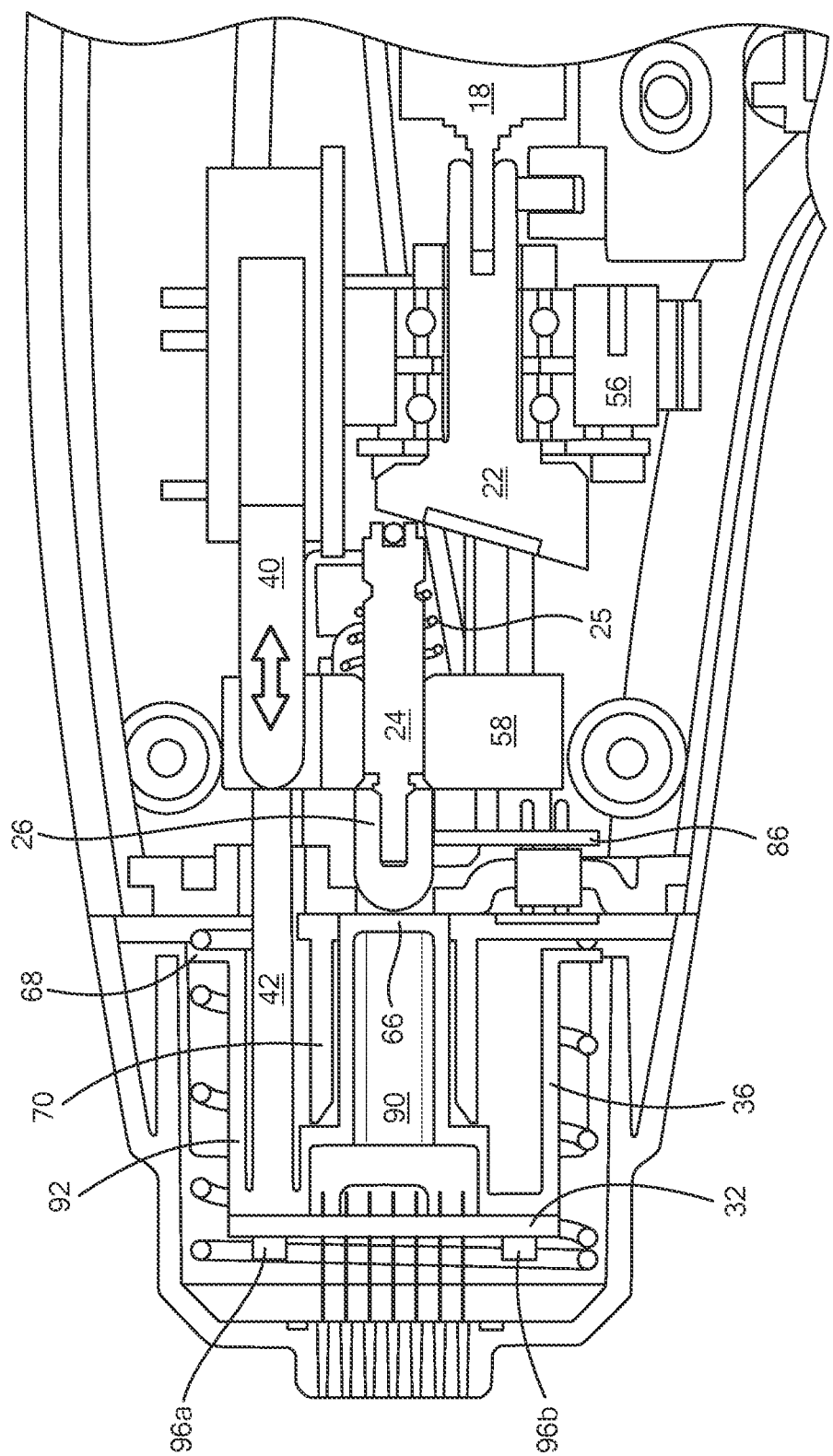
FIG. 11 is a schematic view showing the cartridge assembly of FIG. 10 releasably attached to the handpiece.

As shown in FIGS. 10-11, in a fault case where push rod 24 is determined to be retracted using, for example, the output of a motor encoder, or other sensor, but piston 36 is actually extended, encoder 40 will provide an output signal indicating the piston is extended. The output from the motor encoder or other sensor will indicate the piston is retracted. When these two indications are present, a fault condition exists and the needles may be stuck in the skin, for example. In such a situation, the user (clinician) can be notified and instructed to manually withdraw the needles out of the patient.

The RF applicator described in detail above is energized by an RF generator preferably operated at 1 MHz, although 0.2 to 4 MHz can be used. The RF generator can deliver RF energy between 0.5 to 4 J in steps of 0.5 J, translating to an approximate 10 to 82 mJ of RF energy per needle. In one embodiment, the RF generator can operate from 5 to 27 W depending on tissue impedance. Tissue impedance during RF heating can be determined using a circuit that monitors RF voltage. The RF generator can also deliver precise RF energies independent of tissue impedance by integrating the RF Power determined from real time RF voltage and tissue impedance values. Other embodiments can deliver higher or lower peak RF powers ranging from 5 to 50 W. In another embodiment, a constant power RF generator can be used that is user settable to operate between 0 (purely microneedling) to 5OW (RF microneedling). RF energy can be delivered in a single continuous pulse or can be delivered as subpulses each subpulse delivering 0.5 J with a defined duty cycle using pulse width modulation techniques.

In addition to aiding the delivery of precise RF energies to tissue, the tissue impedance values can be helpful in other ways. For example, the starting impedance can be used to assess the needle insertion plane, as the impedance of fatty tissue is higher than dermal tissue. The ending impedance is typically lower than the starting impedance due to RF heating, so monitoring the magnitude of change is a measure of successful RF heating. Very high starting impedances is a sign that the needles are not penetrating skin alerting the provider to manipulate the tissue via pillowing, folding etc, to achieve good impedance values and thereby good RF energy delivery to tissue. Also, having good starting impedances but ending with high ending impedances is a sign that the needles fell out of tissue during RF delivery alerting the provider to manipulate the tissue via pillowing, folding etc. to achieve good impedance values and thereby good RF energy delivery to tissue.

Although specific features of the invention are shown in some drawings and not in others, this is for convenience only as each feature may be combined with any or all of the other features in accordance with the invention. The words "including," "comprising," "having," and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed; those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A treatment apparatus comprising:
a handpiece housing;
a motorized subsystem in the handpiece housing having a rotating output shaft;
an axial cam driven in rotation by the output shaft;
a push rod linearly driven by the axial cam; and
a cartridge removably attachable to the handpiece housing and including:
a cartridge housing,
a needle assembly,
a piston in the housing engaging the needle assembly and linearly driven forward by the push rod, and
a first biasing member urging the piston rearward; wherein the piston includes an inner member surrounded by an outer cylinder and a wall connecting the inner member to the outer cylinder, the wall engaging the needle assembly; and at least one pogo pin extending between the inner member and the outer cylinder and through the piston end wall.

2. The apparatus of claim 1 in which the motorized subsystem includes a rotary motor driving a gear unit including the rotating output shaft.

3. The apparatus of claim 1 in which the needle assembly includes a printed circuit board with an array of needles extending therefrom.

4. The apparatus of claim 3 in which the cartridge further includes a front face including guiding orifices therethrough for the needles.

5. The apparatus of claim 1 in which the first biasing member includes a spring between the piston and the cartridge housing.

6. The apparatus of claim 1 further including a second biasing member urging the push rod rearward.

7. The apparatus of claim 6 in which the second biasing member includes a spring between the push rod and a push rod guide through which the push rod extends.

8. The apparatus of claim 1 further including a piston fault subsystem.

9. The apparatus of claim 8 in which the piston fault subsystem includes a linear encoder in the handpiece.

10. The apparatus of claim 9 in which the piston fault subsystem further includes a pin extending rearwardly from the piston which engages and drives the linear encoder.

11. The apparatus of claim 1 in which the outer cylinder includes a flange.

12. The apparatus of claim 1 in which the piston end wall further includes one or more posts extending therefrom connected to the needle assembly printed circuit board.

13. The apparatus of claim 1 in which the piston further includes a rearwardly extending post.

14. The apparatus of claim 13 in which the cartridge further includes a rear wall including an orifice for the piston rearwardly extending post and an orifice for the at least one pogo pin.

15. The apparatus of claim 14 in which the cartridge rear wall further includes at least one rearwardly extending snap hook.

16. A treatment apparatus handpiece cartridge comprising:
a housing with a front face and a rear wall;
a needle assembly in the housing including a printed circuit board with a plurality of needles extending therefrom through orifices in the front face of the housing;
a piston movable relative to the housing rear wall and engaging the printed circuit board for driving the needles;
a spring between the piston and the housing front face urging the piston rearward; and
a pair of pogo pins extending from the printed circuit board rearward through the piston and the housing rear wall for energizing the needles; wherein the piston includes an inner member surrounded by an outer cylinder and an end wall connecting the inner member to the outer cylinder, end the wall engaging the needle assembly printed circuit board; and at least one pogo pin extending between the inner member and the outer cylinder and through the piston end wall.

17. The cartridge of claim 16 further including a piston fault subsystem.

18. The cartridge of claim 16 in which the piston fault subsystem includes a pin extending rearwardly from the piston through the housing rear wall for driving a linear encoder.

19. The cartridge of claim 16 in which the outer cylinder includes a flange for the spring.

20. The cartridge of claim 16 in which the piston end wall further includes one or more posts extending therefrom connected to the needle assembly printed circuit board.

21. The cartridge of claim 16 in which the cartridge rear wall further includes at least one rearwardly extending snap hook.

22. A treatment apparatus comprising:
a handpiece housing;
a motorized subsystem in the handpiece housing and having a rotating output shaft;
a cam driven in rotation by the output shaft;
a push rod linearly driven by the cam; and
a cartridge removably attachable to the handpiece housing and including:
  a housing with a front face and a rear wall,
  a needle assembly in the housing including a printed circuit board with a plurality of needles extending therefrom through orifices in the front face of the housing,
  a piston movable relative to the housing rear wall and engaging the printed circuit board for driving the needles,
  a spring between the piston and the housing front face urging the piston rearward, and
  a pair of pogo pins extending from the printed circuit board rearward through the piston and the housing rear wall for energizing the needles; the piston includes an inner member surrounded by an outer cylinder and an end wall connecting the inner member to the outer cylinder, the end wall engaging the needle assembly; and at least one pogo pin extending between the inner member and the outer cylinder and through the piston end wall.

23. The apparatus of claim 22 further including a piston fault subsystem.

24. The apparatus of claim 23 in which the piston fault subsystem includes a linear encoder in the handpiece.

25. The apparatus of claim 24 in which the piston fault subsystem further includes a pin extending rearwardly from the piston and through the housing rear wall and which engages and drives the linear encoder.

26. The apparatus of claim 22 in which the outer cylinder includes a flange for the spring.

27. The apparatus of claim 22 in which the piston end wall further includes one or more posts extending therefrom connected to the needle assembly printed circuit board.

28. The apparatus of claim 23 in which the piston further includes a rearwardly extending post.

29. The apparatus of claim 22 in which the cartridge rear wall further includes at least one rearwardly extending snap hook.

30. The apparatus of claim 22 in which the motorized subsystem includes a rotary motor driving a gear unit including the rotating output shaft.

31. The apparatus of claim 22 further including a spring for retracting the push rod.

* * * * *